(12) United States Patent
Nishida et al.

(10) Patent No.: US 7,927,853 B2
(45) Date of Patent: Apr. 19, 2011

(54) DNA LIGASE MUTANTS

(75) Inventors: Hirokazu Nishida, Kokubunji (JP); Yoshizumi Ishino, Fukuoka (JP); Kosuke Morikawa, Takatsuki (JP)

(73) Assignee: Hitachi, Ltd., Tokyo (JP)

( * ) Notice: Subject to any disclaimer, the term of this patent is extended or adjusted under 35 U.S.C. 154(b) by 785 days.

(21) Appl. No.: 11/473,272

(22) Filed: Jun. 23, 2006

(65) Prior Publication Data

US 2007/0037190 A1    Feb. 15, 2007

(30) Foreign Application Priority Data

Aug. 10, 2005   (JP) .................................. 2005-232360

(51) Int. Cl.
*C12N 9/10* (2006.01)
*C12N 9/00* (2006.01)

(52) U.S. Cl. ........ 435/193; 435/183; 435/91.1; 530/350

(58) Field of Classification Search .................. None
See application file for complete search history.

(56) References Cited

U.S. PATENT DOCUMENTS

| 5,506,137 | A  | * | 4/1996 | Mathur et al. | ............. 435/252.3 |
| 6,280,998 | B1 |   | 8/2001 | Mathur et al. | |
| 6,576,453 | B2 | * | 6/2003 | Barany et al. | ................. 435/193 |

OTHER PUBLICATIONS

Ngo et al. In the Protein Folding Problem and Tertiary Structure Prediction, 1994, Merz et al. (ed.), Birkhauser, Boston, MA, pp. 433 and 492-495.*
Jeon, Sung-Jong, "Development of Extremely Thermostable DNA Ligase for Genetic Diagnosis", AIST Today, vol. 11, Winter 2004, 1 page Abstract, (4 pages in Japanese).

* cited by examiner

*Primary Examiner* — Richard G Hutson
(74) *Attorney, Agent, or Firm* — Stites & Harbison PLLC; Juan Carlos A. Marquez, Esq.

(57) ABSTRACT

It is intended to obtain DNA ligase improved in binding ability and reactivity with DNA, particularly thermostable DNA ligase improved in binding ability and reactivity with DNA. The present invention provides a DNA ligase mutant improved in binding ability and reactivity with DNA, which is obtained by partially or completely deleting a C-terminal helix portion of DNA ligase. Particularly, the mutant is derived from a thermostable bacterium.

3 Claims, 1 Drawing Sheet

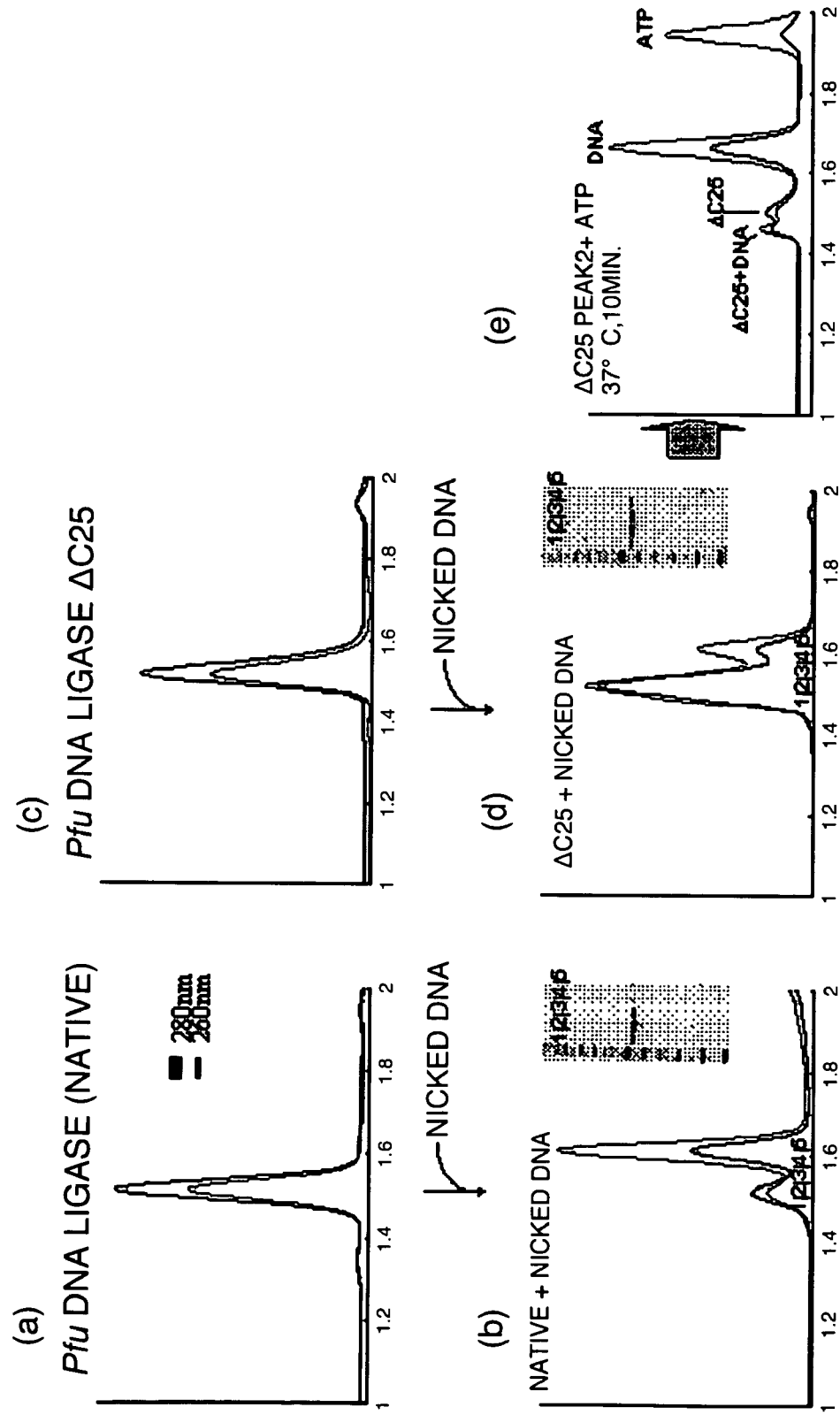

SEQUENCE LISTING

<160> NUMBER OF SEQ ID NOS: 17

<210> SEQ ID NO 1
<211> LENGTH: 1683
<212> TYPE: DNA
<213> ORGANISM: Pyrococcus furiosus

<400> SEQUENCE: 1

| | | | | | |
|---|---|---|---|---|---|
| atgaggtatc | tagagcttgc | tcaactttat | caaaagttag | aaaagacaac | tatgaaactt | 60 |
| ataaagacta | gacttgtcgc | cgacttcctg | aaaaaagtac | cagatgatca | tctggagttc | 120 |
| attccctatc | taattcttgg | agaagttttt | ccagagtggg | atgaaaggga | gctgggtgtg | 180 |
| ggagaaaagc | tgttaattaa | agctgtagca | atggccactg | gaattgacgc | aaaagaaatc | 240 |
| gaagagtctg | taaaagatac | tggagacctt | ggagagagca | tagccttagc | tgtaaagaaa | 300 |
| aagaagcaga | gagcttcttc | tctcagccc | ctcacaataa | agagggtata | tcaaacccttt | 360 |
| gtaaaggttg | cagaaacaac | gggggaggga | agccaagata | aaaagtaaa | gtatctagct | 420 |
| gatttgttca | tggacgcaga | acctttagaa | gctaagtatc | ttgctcgtac | aatcttagga | 480 |
| acaatgagaa | caggagttgc | agaaggattg | cttagagatg | caatagcaat | ggcattccac | 540 |
| gtaaaggtag | agcttgttga | gagagcttac | atgctaacga | gtgatttcgg | atatgtagct | 600 |
| aaaatagcaa | agcttgaagg | aaatgaaggg | ctagcaaaag | ttcaagttca | actcggaaag | 660 |
| ccaataaagc | caatgcttgc | ccagcaagct | gctagcataa | gagatgcact | tctcgagatg | 720 |
| ggtggagagg | cagagttcga | gattaaatac | gatggagcaa | gggtgcaggt | gcacaaggat | 780 |
| ggctcaaaaa | ttatagtcta | ttctagaaga | ctggagaacg | tcaccagagc | gattccagaa | 840 |
| attgttgagg | ctctaaaaga | ggcaataata | cctgaaaagg | caatagtgga | aggagaactt | 900 |
| gtggcaattg | gagaaaacgg | aagaccattg | cccttccaat | atgtgcttag | aaggtttagg | 960 |
| agaaagcata | acatagaaga | aatgatggaa | aagatacctc | tcgagctcaa | cttattcgac | 1020 |
| gttctctacg | tagatggaca | aagcttgatt | gacactaagt | tcattgatag | aagaagaaca | 1080 |
| cttgaagaaa | taataaagca | gaatgaaaag | ataaggtag | cagaaaacct | aataacaaag | 1140 |
| aaagtcgagg | aagcagaggc | attttacaag | agagcactcg | aaatgggga | cgagggattg | 1200 |
| atggccaaga | ggttagatgc | agtctacgaa | ccaggtaaca | gaggaaagaa | gtggttgaag | 1260 |
| ataaagccca | caatggagaa | cttagattta | gtaatcatag | agcagaatg | gggagaggga | 1320 |
| agaagagccc | atctctttgg | ttcattcatc | ctgggagcat | atgatccaga | aacaggagaa | 1380 |
| ttcctagagg | taggaaaagt | gggaagtgga | ttcacagatg | atgacttagt | tgagtttacg | 1440 |
| aagatgctaa | agccccttat | tataaaagag | gaaggaaaga | gagtctggct | ccagcccaaa | 1500 |
| gttgttattg | aagtgacata | tcaagaaatt | cagaagagtc | caaaatacag | aagtggattt | 1560 |
| gcattaaggt | tcccaaggtt | cgttgcactt | agagatgata | aaggaccaga | gatgcagat | 1620 |
| acaatagaga | gaatcgcaca | actttacgag | ttgcaagaaa | agatgaaagg | aaaagtggaa | 1680 |
| agc | | | | | | 1683 |

<210> SEQ ID NO 2
<211> LENGTH: 561
<212> TYPE: PRT
<213> ORGANISM: Pyrococcus furiosus

<400> SEQUENCE: 2

Met Arg Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
            20                  25                  30

Val Pro Asp His Leu Glu Phe Ile Pro Tyr Leu Ile Leu Gly Glu
            35                  40                  45

Val Phe Pro Glu Trp Asp Arg Glu Leu Gly Val Gly Glu Lys Leu
 50                          55                  60

Leu Ile Lys Ala Val Ala Met Ala Thr Gly Ile Asp Ala Lys Glu Ile
 65                  70                  75                  80

Glu Glu Ser Val Lys Asp Thr Gly Asp Leu Gly Glu Ser Ile Ala Leu
                85                  90                  95

Ala Val Lys Lys Lys Gln Lys Ser Phe Phe Ser Gln Pro Leu Thr
                100                 105                 110

Ile Lys Arg Val Tyr Gln Thr Leu Val Lys Val Ala Glu Thr Thr Gly
            115                 120                 125

Glu Gly Ser Gln Asp Lys Lys Val Lys Tyr Leu Ala Asp Leu Phe Met
 130                 135                 140

Asp Ala Glu Pro Leu Glu Ala Lys Tyr Leu Ala Arg Thr Ile Leu Gly
145                 150                 155                 160

Thr Met Arg Thr Gly Val Ala Glu Gly Leu Leu Arg Asp Ala Ile Ala
            165                 170                 175

Met Ala Phe His Val Lys Val Glu Leu Val Glu Arg Ala Tyr Met Leu
            180                 185                 190

Thr Ser Asp Phe Gly Tyr Val Ala Lys Ile Ala Lys Leu Glu Gly Asn
            195                 200                 205

Glu Gly Leu Ala Lys Val Gln Val Gln Leu Gly Lys Pro Ile Lys Pro
 210                 215                 220

Met Leu Ala Gln Gln Ala Ala Ser Ile Arg Asp Ala Leu Leu Glu Met
225                 230                 235                 240

Gly Gly Glu Ala Glu Phe Glu Ile Lys Tyr Asp Gly Ala Arg Val Gln
            245                 250                 255

Val His Lys Asp Gly Ser Lys Ile Ile Val Tyr Ser Arg Arg Leu Glu
            260                 265                 270

Asn Val Thr Arg Ala Ile Pro Glu Ile Val Glu Ala Leu Lys Glu Ala
            275                 280                 285

Ile Ile Pro Glu Lys Ala Ile Val Glu Gly Leu Val Ala Ile Gly
            290                 295                 300

Glu Asn Gly Arg Pro Leu Pro Phe Gln Tyr Val Leu Arg Arg Phe Arg
305                 310                 315                 320

Arg Lys His Asn Ile Glu Glu Met Met Glu Lys Ile Pro Leu Glu Leu
                325                 330                 335

Asn Leu Phe Asp Val Leu Tyr Val Asp Gly Gln Ser Leu Ile Asp Thr
            340                 345                 350

Lys Phe Ile Asp Arg Arg Thr Leu Glu Glu Ile Ile Lys Gln Asn
            355                 360                 365

Glu Lys Ile Lys Val Ala Glu Asn Leu Ile Thr Lys Lys Val Glu Glu
 370                 375                 380

Ala Glu Ala Phe Tyr Lys Arg Ala Leu Glu Met Gly His Glu Gly Leu
385                 390                 395                 400

Met Ala Lys Arg Leu Asp Ala Val Tyr Glu Pro Gly Asn Arg Gly Lys
                405                 410                 415

Lys Trp Leu Lys Ile Lys Pro Thr Met Glu Asn Leu Asp Leu Val Ile
            420                 425                 430

Ile Gly Ala Glu Trp Gly Glu Gly Arg Arg Ala His Leu Phe Gly Ser

```
                435             440             445
Phe Ile Leu Gly Ala Tyr Asp Pro Glu Thr Gly Glu Phe Leu Glu Val
            450                 455                 460
Gly Lys Val Gly Ser Gly Phe Thr Asp Asp Leu Val Glu Phe Thr
465             470                 475                 480
Lys Met Leu Lys Pro Leu Ile Ile Lys Glu Glu Gly Lys Arg Val Trp
                485                 490                 495
Leu Gln Pro Lys Val Val Ile Glu Val Thr Tyr Gln Glu Ile Gln Lys
                500                 505                 510
Ser Pro Lys Tyr Arg Ser Gly Phe Ala Leu Arg Phe Pro Arg Phe Val
                515                 520                 525
Ala Leu Arg Asp Asp Lys Gly Pro Glu Asp Ala Asp Thr Ile Glu Arg
                530                 535                 540
Ile Ala Gln Leu Tyr Glu Leu Gln Glu Lys Met Lys Gly Lys Val Glu
545                 550                 555                 560
Ser
```

```
<210> SEQ ID NO 3
<211> LENGTH: 1683
<212> TYPE: DNA
<213> ORGANISM: Pyrococcus furiosus

<400> SEQUENCE: 3
atgaggtatc tagagcttgc tcaactttat caaaagttag aaaagacaac tatgaaactt      60
ataaagacta gacttgtcgc cgacttcctg aaaaaagtac agatgatca tctggagttc     120
attccctatc taattcttgg agaagttttt ccagagtggg atgaaaggga gctgggtgtg     180
ggagaaaagc tgttaattaa agctgtagca atggccactg gaattgacgc aaaagaaatc     240
gaagagtctg taaagatac tggagacctt ggagagagca tagccttagc tgtaaagaaa      300
aagaagcaga gagcttcttc tctcagccc tcacaataa agagggtata tcaaaccctt       360
gtaaaggttg cagaaacaac gggggaggga agccaagata aaaagtaaa gtatctagct      420
gatttgttca tggacgcaga acctttagaa gctaagtatc ttgctcgtac aatcttagga     480
acaatgagaa caggagttgc agaaggattg cttagagatg caatagcaat ggcattccac     540
gtaaaggtag agcttgttga gagagcttac atgctaacga gtgatttcgg atatgtagct     600
aaaatagcaa agcttgaagg aaatgaaggg ctagcaaaag ttcaagttca actcggaaag     660
ccaataaagc caatgcttgc ccagcaagct gctagcataa gagatgcact tctcgagatg     720
ggtggagagg cagagttcga gattaaatac gatggagcaa gggtgcaggt gcacaaggat     780
ggctcaaaaa ttatagtcta ttctagaaga ctggagaacg tcaccagagc gattccagaa     840
attgttgagg ctctaaaaga ggcaataata cctgaaaagg caatagtgga aggagaactt     900
gtggcaattg agaaaacgg aagaccattg cccttccaat atgtgcttag aaggtttagg     960
agaaagcata acatagaaga aatgatggaa aagataccct cgagctcaa cttattcgac    1020
gttctctacg tagatggaca aagcttgatt gacactaagt tcattgatag aagaagaaca    1080
cttgaagaaa taataaagca gaatgaaaag ataaggtag cagaaaacct aataacaaag    1140
aaagtcgagg aagcagaggc attttacaag agagcactcg aaatggggca cgagggattg    1200
atggccaaga ggttagatgc agtctacgaa ccaggtaaca gaggaaagaa gtggttgaag   1260
ataaagccca aatggagaa cttagattta gtaatcatag gagcagaatg gggagaggga    1320
agaagagccc atctctttgg ttcattcatc ctggagcat atgatccaga aacaggagaa    1380
ttcctagagg taggaaaagt gggaagtgga ttcacagatg atgacttagt tgagtttacg    1440
```

-continued

```
aagatgctaa agccccttat tataaaagag gaaggaaaga gagtctggct ccagcccaaa    1500
gttgttattg aagtgacata tcaagaaatt cagaagagtc caaaatacag aagtggattt    1560
gcattaaggt tcccaaggtt cgttgcactt agagatgata aaggaccaga agatgcagat    1620
acaatagaga gaatcgcaca actttacgag ttgcaagaaa agatgaaagg aaaagtggaa    1680
agc                                                                  1683
```

<210> SEQ ID NO 4
<211> LENGTH: 561
<212> TYPE: PRT
<213> ORGANISM: Pyrococcus furiosus

<400> SEQUENCE: 4

```
Met Gly Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
                20                  25                  30

Val Pro Asp Asp His Leu Glu Phe Ile Pro Tyr Leu Ile Leu Gly Glu
            35                  40                  45

Val Phe Pro Glu Trp Asp Glu Arg Leu Gly Val Gly Glu Lys Leu
        50                  55                  60

Leu Ile Lys Ala Val Ala Met Ala Thr Gly Ile Asp Ala Lys Glu Ile
65                  70                  75                  80

Glu Glu Ser Val Lys Asp Thr Gly Asp Leu Gly Glu Ser Ile Ala Leu
                85                  90                  95

Ala Val Lys Lys Lys Lys Gln Lys Ser Phe Phe Ser Gln Pro Leu Thr
            100                 105                 110

Ile Lys Arg Val Tyr Gln Thr Leu Val Lys Val Ala Glu Thr Thr Gly
        115                 120                 125

Glu Gly Ser Gln Asp Lys Lys Val Lys Tyr Leu Ala Asp Leu Phe Met
    130                 135                 140

Asp Ala Glu Pro Leu Glu Ala Lys Tyr Leu Ala Arg Thr Ile Leu Gly
145                 150                 155                 160

Thr Met Arg Thr Gly Val Ala Glu Gly Leu Leu Arg Asp Ala Ile Ala
                165                 170                 175

Met Ala Phe His Val Lys Val Glu Leu Val Glu Arg Ala Tyr Met Leu
            180                 185                 190

Thr Ser Asp Phe Gly Tyr Val Ala Lys Ile Ala Lys Leu Glu Gly Asn
        195                 200                 205

Glu Gly Leu Ala Lys Val Gln Val Gln Leu Gly Lys Pro Ile Lys Pro
    210                 215                 220

Met Leu Ala Gln Gln Ala Ala Ser Ile Arg Asp Ala Leu Leu Glu Met
225                 230                 235                 240

Gly Gly Glu Ala Glu Phe Glu Ile Lys Tyr Asp Gly Ala Arg Val Gln
                245                 250                 255

Val His Lys Asp Gly Ser Lys Ile Ile Val Tyr Ser Arg Arg Leu Glu
            260                 265                 270

Asn Val Thr Arg Ala Ile Pro Glu Ile Val Glu Ala Leu Lys Glu Ala
        275                 280                 285

Ile Ile Pro Glu Lys Ala Ile Val Glu Gly Leu Val Ala Ile Gly
    290                 295                 300

Glu Asn Gly Arg Pro Leu Pro Phe Gln Tyr Val Leu Arg Arg Phe Arg
305                 310                 315                 320

Arg Lys His Asn Ile Glu Glu Met Met Glu Lys Ile Pro Leu Glu Leu
```

```
                  325                 330                 335
Asn Leu Phe Asp Val Leu Tyr Val Asp Gly Gln Ser Leu Ile Asp Thr
            340                 345                 350
Lys Phe Ile Asp Arg Arg Thr Leu Glu Glu Ile Ile Lys Gln Asn
        355                 360                 365
Glu Lys Ile Lys Val Ala Glu Asn Leu Ile Thr Lys Val Glu Glu
    370                 375                 380
Ala Glu Ala Phe Tyr Lys Arg Ala Leu Glu Met Gly His Glu Gly Leu
385                 390                 395                 400
Met Ala Lys Arg Leu Asp Ala Val Tyr Glu Pro Gly Asn Arg Gly Lys
                405                 410                 415
Lys Trp Leu Lys Ile Lys Pro Thr Met Glu Asn Leu Asp Leu Val Ile
            420                 425                 430
Ile Gly Ala Glu Trp Gly Glu Gly Arg Arg Ala His Leu Phe Gly Ser
        435                 440                 445
Phe Ile Leu Gly Ala Tyr Asp Pro Glu Thr Gly Glu Phe Leu Glu Val
    450                 455                 460
Gly Lys Val Gly Ser Gly Phe Thr Asp Asp Leu Val Glu Phe Thr
465                 470                 475                 480
Lys Met Leu Lys Pro Leu Ile Ile Lys Glu Glu Gly Lys Arg Val Trp
                485                 490                 495
Leu Gln Pro Lys Val Val Ile Glu Val Thr Tyr Gln Glu Ile Gln Lys
            500                 505                 510
Ser Pro Lys Tyr Arg Ser Gly Phe Ala Leu Arg Phe Pro Arg Phe Val
        515                 520                 525
Ala Leu Arg Asp Asp Lys Gly Pro Glu Asp Ala Asp Thr Ile Glu Arg
    530                 535                 540
Ile Ala Gln Leu Tyr Glu Leu Gln Glu Lys Met Lys Gly Lys Val Glu
545                 550                 555                 560
Ser

<210> SEQ ID NO 5
<211> LENGTH: 1608
<212> TYPE: DNA
<213> ORGANISM: Pyrococcus furiosus

<400> SEQUENCE: 5
atgaggtatc tagagcttgc tcaactttat caaaagttag aaaagacaac tatgaaactt      60
ataaagacta gacttgtcgc cgacttcctg aaaaaagtac agatgatca tctggagttc     120 attccctatc taattcttgg agaagttttt ccagagtggg atgaaaggga gctgggtgtg     180
ggagaaaagc tgttaattaa agctgtagca atggccactg gaattgacgc aaaagaaatc     240
gaagagtctg taaagatac tggagacctt ggagagagca tagccttagc tgtaaagaaa      300
aagaagcaga gagcttctt ctctcagccc ctcacaataa agagggtata tcaaaccctt      360
gtaaaggttg cagaaacaac gggggaggga agccaagata aaaagtaaa gtatctagct      420 gatttgttca tggacgcaga acctttagaa gctaagtatc ttgctcgtac aatcttagga     480
acaatgagaa caggagttgc agaaggattg cttagagatg caatagcaat ggcattccac     540
gtaaaggtag agcttgttga gagagcttac atgctaacga gtgatttcgg atatgtagct     600
aaaatagcaa agcttgaagg aaatgaaggg ctagcaaaag ttcaagttca actcggaaag     660
ccaataaagc caatgcttgc ccagcaagct gctagcataa agatgcact tctcgagatg      720 ggtggagagg cagagttcga gattaaatac gatggagcaa gggtgcaggt gcacaaggat     780
```

```
ggctcaaaaa ttatagtcta ttctagaaga ctggagaacg tcaccagagc gattccagaa    840
attgttgagg ctctaaaaga ggcaataata cctgaaaagg caatagtgga aggagaactt    900
gtggcaattg agaaaacgg aagaccattg cccttccaat atgtgcttag aaggtttagg    960
agaaagcata acatagaaga aatgatgaa aagatacctc tcgagctcaa cttattcgac   1020
gttctctacg tagatggaca aagcttgatt gacactaagt tcattgatag aagaagaaca   1080
cttgaagaaa taataaagca gaatgaaaag ataaaggtag cagaaaacct aataacaaag   1140
aaagtcgagg aagcagaggc attttacaag agagcactcg aaatgggca cgagggattg   1200 atggccaaga ggttagatgc agtctacgaa ccaggtaaca gaggaaagaa gtggttgaag   1260
ataaagccca caatggagaa cttagattta gtaatcatag gagcagaatg gggagaggga   1320
agaagagccc atctctttgg ttcattcatc ctgggagcat atgatccaga aacaggagaa   1380
ttcctagagg taggaaaagt gggaagtgga ttcacagatg atgacttagt tgagtttacg   1440
aagatgctaa agcccttat tataaaagag gaaggaaaga gagtctggct ccagcccaaa   1500
gttgttattg aagtgacata tcaagaaatt cagaagagtc caaaatacag aagtggattt   1560
gcattaaggt tcccaaggtt cgttgcactt agagatgata aaggacca              1608
```

<210> SEQ ID NO 6
<211> LENGTH: 536
<212> TYPE: PRT
<213> ORGANISM: Pyrococcus furiosus

<400> SEQUENCE: 6

```
Met Gly Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
            20                  25                  30

Val Pro Asp Asp His Leu Glu Phe Ile Pro Tyr Leu Ile Leu Gly Glu
        35                  40                  45

Val Phe Pro Glu Trp Asp Glu Arg Leu Gly Val Gly Glu Lys Leu
    50                  55                  60

Leu Ile Lys Ala Val Ala Met Ala Thr Gly Ile Asp Ala Lys Glu Ile
65                  70                  75                  80

Glu Glu Ser Val Lys Asp Thr Gly Asp Leu Gly Glu Ser Ile Ala Leu
                85                  90                  95

Ala Val Lys Lys Lys Gln Lys Ser Phe Phe Ser Gln Pro Leu Thr
            100                 105                 110

Ile Lys Arg Val Tyr Gln Thr Leu Val Lys Val Ala Glu Thr Thr Gly
        115                 120                 125

Glu Gly Ser Gln Asp Lys Lys Val Lys Tyr Leu Ala Asp Leu Phe Met
    130                 135                 140

Asp Ala Glu Pro Leu Glu Ala Lys Tyr Leu Ala Arg Thr Ile Leu Gly
145                 150                 155                 160

Thr Met Arg Thr Gly Val Ala Glu Gly Leu Leu Arg Asp Ala Ile Ala
                165                 170                 175

Met Ala Phe His Val Lys Val Glu Leu Val Glu Arg Ala Tyr Met Leu
            180                 185                 190

Thr Ser Asp Phe Gly Tyr Val Ala Lys Ile Ala Lys Leu Glu Gly Asn
        195                 200                 205

Glu Gly Leu Ala Lys Val Gln Val Gln Leu Gly Lys Pro Ile Lys Pro
    210                 215                 220

Met Leu Ala Gln Gln Ala Ala Ser Ile Arg Asp Ala Leu Leu Glu Met
225                 230                 235                 240
```

```
Gly Gly Glu Ala Glu Phe Glu Ile Lys Tyr Asp Gly Ala Arg Val Gln
            245                 250                 255

Val His Lys Asp Gly Ser Lys Ile Ile Val Tyr Ser Arg Arg Leu Glu
        260                 265                 270

Asn Val Thr Arg Ala Ile Pro Glu Ile Val Glu Ala Leu Lys Glu Ala
    275                 280                 285

Ile Ile Pro Glu Lys Ala Ile Val Gly Glu Leu Val Ala Ile Gly
290                 295                 300

Glu Asn Gly Arg Pro Leu Pro Phe Gln Tyr Val Leu Arg Arg Phe Arg
305                 310                 315                 320

Arg Lys His Asn Ile Glu Met Met Glu Lys Ile Pro Leu Glu Leu
                325                 330                 335

Asn Leu Phe Asp Val Leu Tyr Val Asp Gly Gln Ser Leu Ile Asp Thr
            340                 345                 350

Lys Phe Ile Asp Arg Arg Thr Leu Glu Glu Ile Ile Lys Gln Asn
        355                 360                 365

Glu Lys Ile Lys Val Ala Glu Asn Leu Ile Thr Lys Lys Val Glu Glu
    370                 375                 380

Ala Glu Ala Phe Tyr Lys Arg Ala Leu Glu Met Gly His Glu Gly Leu
385                 390                 395                 400

Met Ala Lys Arg Leu Asp Ala Val Tyr Glu Pro Gly Asn Arg Gly Lys
                405                 410                 415

Lys Trp Leu Lys Ile Lys Pro Thr Met Glu Asn Leu Asp Leu Val Ile
            420                 425                 430

Ile Gly Ala Glu Trp Gly Glu Gly Arg Arg Ala His Leu Phe Gly Ser
        435                 440                 445

Phe Ile Leu Gly Ala Tyr Asp Pro Glu Thr Gly Glu Phe Leu Glu Val
    450                 455                 460

Gly Lys Val Gly Ser Gly Phe Thr Asp Asp Leu Val Glu Phe Thr
465                 470                 475                 480

Lys Met Leu Lys Pro Leu Ile Ile Lys Glu Glu Gly Lys Arg Val Trp
                485                 490                 495

Leu Gln Pro Lys Val Val Ile Glu Val Thr Tyr Gln Glu Ile Gln Lys
            500                 505                 510

Ser Pro Lys Tyr Arg Ser Gly Phe Ala Leu Arg Phe Pro Arg Phe Val
        515                 520                 525

Ala Leu Arg Asp Asp Lys Gly Pro
    530                 535

<210> SEQ ID NO 7
<211> LENGTH: 1617
<212> TYPE: DNA
<213> ORGANISM: Pyrococcus furiosus

<400> SEQUENCE: 7
atgaggtatc tagagcttgc tcaactttat caaaagttag aaaagacaac tatgaaactt      60
ataaagacta gacttgtcgc cgacttcctg aaaaaagtac cagatgatca tctggagttc     120
attccctatc taattcttgg agaagttttt ccagagtggg atgaaaggga gctgggtgtg     180
ggagaaaagc tgttaattaa agctgtagca atgccactg gaattgacgc aaaagaaatc     240
gaagagtctg taaagatac tggagacctt ggagagagca tagccttagc tgtaaagaaa     300
aagaagcaga gagcttctt ctctcagccc ctcacaataa agagggtata tcaaccctt      360 gtaaaggttg cagaaacaac gggggaggga agccaagata aaaagtaaa gtatctagct     420
```

```
gatttgttca tggacgcaga acctttagaa gctaagtatc ttgctcgtac aatcttagga   480
acaatgagaa caggagttgc agaaggattg cttagagatg caatagcaat ggcattccac   540
gtaaaggtag agcttgttga gagagcttac atgctaacga gtgatttcgg atatgtagct   600
aaaatagcaa agcttgaagg aaatgaaggg ctagcaaaag ttcaagttca actcggaaag   660
ccaataaagc caatgcttgc ccagcaagct gctagcataa gagatgcact tctcgagatg   720
ggtggagagg cagagttcga gattaaatac gatggagcaa gggtgcaggt gcacaaggat   780
ggctcaaaaa ttatagtcta ttctagaaga ctggagaacg tcaccagagc gattccagaa   840
attgttgagc tctaaaagag gcaataata cctgaaaagg caatagtgga aggagaactt   900
gtggcaattg agaaaacgg aagaccattg cccttccaat atgtgcttag aaggtttagg   960
agaaagcata acatagaaga aatgatgaaa aagatacctc tcgagctcaa cttattcgac  1020
gttctctacg tagatggaca aagcttgatt gacactaagt tcattgatag aagaagaaca  1080
cttgaagaaa taataaagca gaatgaaaag ataaaggtag cagaaaacct aataacaaag  1140
aaagtcgagg aagcagaggc attttacaag agagcactcg aaatggggca cgagggattg  1200
atggccaaga ggttagatgc agtctacgaa ccagtaaca gaggaaagaa gtggttgaag  1260
ataaagccca caatggagaa cttagattta gtaatcatag gagcagaatg gggagaggga  1320
agaagagccc atctctttgg ttcattcatc ctggggagcat atgatccaga acaggagaa   1380
ttcctagagg taggaaaagt gggaagtgga ttcacagatg atgacttagt tgagtttacg  1440
aagatgctaa agcccttat tataaaagag gaaggaaaga gagtctggct ccagcccaaa  1500
gttgttattg aagtgacata tcaagaaatt cagaagagtc caaatacag aagtggatttt 1560
gcattaaggt tcccaaggtt cgttgcactt agagatgata aaggaccaga agatgca     1617
```

<210> SEQ ID NO 8
<211> LENGTH: 539
<212> TYPE: PRT
<213> ORGANISM: Pyrococcus furiosus
<400> SEQUENCE: 8

```
Met Gly Tyr Leu Glu Leu Ala Gln Leu Tyr Gln Lys Leu Glu Lys Thr
1               5                   10                  15

Thr Met Lys Leu Ile Lys Thr Arg Leu Val Ala Asp Phe Leu Lys Lys
            20                  25                  30

Val Pro Asp Asp His Leu Glu Phe Ile Pro Tyr Leu Ile Leu Gly Glu
        35                  40                  45

Val Phe Pro Glu Trp Asp Glu Arg Glu Leu Gly Val Gly Glu Lys Leu
    50                  55                  60

Leu Ile Lys Ala Val Ala Met Ala Thr Gly Ile Asp Ala Lys Glu Ile
65                  70                  75                  80

Glu Glu Ser Val Lys Asp Thr Gly Asp Leu Gly Glu Ser Ile Ala Leu
                85                  90                  95

Ala Val Lys Lys Lys Gln Lys Ser Phe Phe Ser Gln Pro Leu Thr
            100                 105                 110

Ile Lys Arg Val Tyr Gln Thr Leu Val Lys Val Ala Glu Thr Thr Gly
        115                 120                 125

Glu Gly Ser Gln Asp Lys Lys Val Lys Tyr Leu Ala Asp Leu Phe Met
    130                 135                 140

Asp Ala Glu Pro Leu Glu Ala Lys Tyr Leu Ala Arg Thr Ile Leu Gly
145                 150                 155                 160

Thr Met Arg Thr Gly Val Ala Glu Gly Leu Leu Arg Asp Ala Ile Ala
                165                 170                 175
```

-continued

Met Ala Phe His Val Lys Val Glu Leu Val Glu Arg Ala Tyr Met Leu
            180                 185                 190

Thr Ser Asp Phe Gly Tyr Val Ala Lys Ile Ala Lys Leu Glu Gly Asn
            195                 200                 205

Glu Gly Leu Ala Lys Val Gln Val Gln Leu Gly Lys Pro Ile Lys Pro
210                 215                 220

Met Leu Ala Gln Gln Ala Ala Ser Ile Arg Asp Ala Leu Leu Glu Met
225                 230                 235                 240

Gly Gly Glu Ala Glu Phe Glu Ile Lys Tyr Asp Gly Ala Arg Val Gln
                245                 250                 255

Val His Lys Asp Gly Ser Lys Ile Ile Val Tyr Ser Arg Arg Leu Glu
            260                 265                 270

Asn Val Thr Arg Ala Ile Pro Glu Ile Val Glu Ala Leu Lys Glu Ala
            275                 280                 285

Ile Ile Pro Glu Lys Ala Ile Val Gly Glu Leu Val Ala Ile Gly
            290                 295                 300

Glu Asn Gly Arg Pro Leu Pro Phe Gln Tyr Val Leu Arg Arg Phe Arg
305                 310                 315                 320

Arg Lys His Asn Ile Glu Glu Met Met Glu Lys Ile Pro Leu Glu Leu
                325                 330                 335

Asn Leu Phe Asp Val Leu Tyr Val Asp Gly Gln Ser Leu Ile Asp Thr
            340                 345                 350

Lys Phe Ile Asp Arg Arg Thr Leu Glu Glu Ile Ile Lys Gln Asn
            355                 360                 365

Glu Lys Ile Lys Val Ala Glu Asn Leu Ile Thr Lys Lys Val Glu Glu
370                 375                 380

Ala Glu Ala Phe Tyr Lys Arg Ala Leu Glu Met Gly His Glu Gly Leu
385                 390                 395                 400

Met Ala Lys Arg Leu Asp Ala Val Tyr Glu Pro Gly Asn Arg Gly Lys
            405                 410                 415

Lys Trp Leu Lys Ile Lys Pro Thr Met Glu Asn Leu Asp Leu Val Ile
            420                 425                 430

Ile Gly Ala Glu Trp Gly Glu Gly Arg Arg Ala His Leu Phe Gly Ser
            435                 440                 445

Phe Ile Leu Gly Ala Tyr Asp Pro Glu Thr Gly Glu Phe Leu Glu Val
            450                 455                 460

Gly Lys Val Gly Ser Gly Phe Thr Asp Asp Leu Val Glu Phe Thr
465                 470                 475                 480

Lys Met Leu Lys Pro Leu Ile Ile Lys Glu Glu Gly Lys Arg Val Trp
            485                 490                 495

Leu Gln Pro Lys Val Val Ile Glu Val Thr Tyr Gln Glu Ile Gln Lys
            500                 505                 510

Ser Pro Lys Tyr Arg Ser Gly Phe Ala Leu Arg Phe Pro Arg Phe Val
            515                 520                 525

Ala Leu Arg Asp Asp Lys Gly Pro Glu Asp Ala
530                 535

<210> SEQ ID NO 9
<211> LENGTH: 25
<212> TYPE: DNA
<213> ORGANISM: Pyrococcus furiosus

<400> SEQUENCE: 9
ctagtggatc tgatgcgtta tctgg    25

```
<210> SEQ ID NO 10
<211> LENGTH: 24
<212> TYPE: DNA
<213> ORGANISM: Pyrococcus furiosus

<400> SEQUENCE: 10
tcgggactat tgttagacct tagc                                              24

<210> SEQ ID NO 11
<211> LENGTH: 29
<212> TYPE: DNA
<213> ORGANISM: Pyrococcus furiosus

<400> SEQUENCE: 11
ggccatgggt tatctggagc ttgctcaac                                         29

<210> SEQ ID NO 12
<211> LENGTH: 32
<212> TYPE: DNA
<213> ORGANISM: Pyrococcus furiosus

<400> SEQUENCE: 12
gcggatcctt agctttccac ttttctttca tc                                     32

<210> SEQ ID NO 13
<211> LENGTH: 30
<212> TYPE: DNA
<213> ORGANISM: Pyrococcus furiosus

<400> SEQUENCE: 13
ccagaagatg cataaacaat agagagaatc                                        30

<210> SEQ ID NO 14
<211> LENGTH: 30
<212> TYPE: DNA
<213> ORGANISM: Pyrococcus furiosus

<400> SEQUENCE: 14
gattctctct attgtttatg catcttctgg                                        30

<210> SEQ ID NO 15
<211> LENGTH: 30
<212> TYPE: DNA
<213> ORGANISM: Pyrococcus furiosus

<400> SEQUENCE: 15
gataaaggac cataagatgc agatacaata                                        30

<210> SEQ ID NO 16
<211> LENGTH: 30
<212> TYPE: DNA
<213> ORGANISM: Pyrococcus furiosus

<400> SEQUENCE: 16
tattgtatct gcatcttatg gtcctttatc                                        30

<210> SEQ ID NO 17
<211> LENGTH: 30
<212> TYPE: DNA
<213> ORGANISM: Pyrococcus furiosus

<400> SEQUENCE: 17
tatagcgaag ctatatatag cgaagctata                                        30
```

DNA LIGASE MUTANTS

INCORPORATION BY REFERENCE

The present application claims priority from Japanese application JP 2005-232360 filed on Aug. 10, 2005, the content of which is hereby incorporated by reference into this application.

FIELD OF THE INVENTION

The present invention relates to a DNA ligase mutant. In particular, the present invention relates to a DNA ligase mutant improved in DNA-binding ability, which is obtained by partially or completely deleting a C-terminal helix portion of DNA ligase, to DNA encoding the mutant, and to the use of the mutant.

BACKGROUND OF THE INVENTION

DNA ligase is an enzyme having an activity of linking between the 3'-OH group of a DNA strand and the 5'-phosphate group of another DNA strand through phosphodiester bond and participates in DNA replication and repair in vivo. In recent years, Ligase Chain Reaction (LCR) method has been developed and used as a novel gene amplification technique. The LCR method is a method of amplifying or detecting target genes by way of thermal cycling reaction using thermostable DNA ligase. For enhancing the efficiency of the LCR method, additional thermostable ligase has been explored and has been available commercially. DNA ligase derived from a hyperthermophilic archaebacterium has been found very recently (see the press release dated Sep. 10, 2003, as titled "Success in Development of the Most Thermostable Enzyme (DNA Ligase) in the World", on website of National Institute of Advanced Industrial Science and Technology at http://www.aist.go.jp/aist_j/press_release/pr2003/pr200 30910/pr20030910.html). However, these thermostable DNA ligases exhibit exceedingly low DNA-binding ability. On the other hand, DNA ligase derived from a phage is known as an enzyme having high DNA-binding ability. However, this DNA ligase has poor thermostability and therefore, is not suitable for the LCR method. Accordingly, DNA ligase with excellent thermostability and DNA-binding ability and reactivity capable of efficiently performing the LCR method at a sufficient reaction rate has not been found yet.

BRIEF SUMMARY OF THE INVENTION

A problem to be solved by the present invention is to obtain DNA ligase improved in DNA-binding property, particularly thermostable DNA ligase improved in DNA-binding property.

Other objects, features and advantages of the invention will become apparent from the following description of the embodiments of the invention taken in conjunction with the accompanying drawings.

BRIEF DESCRIPTION OF THE DRAWINGS

FIG. 1 is a diagram showing a result of examining the binding ability between untreated (wild type: WT) DNA ligase and substrate DNA, the binding ability between a DNA ligase mutant (ΔC25) of the present invention and substrate DNA, and the reaction between the DNA ligase mutant (ΔC25) of the present invention and substrate DNA. In the drawing, "Pfu" represents *Pyrococcus furiosus*. The result obtained by using the WT ligase is shown in panels (a) and (b) in FIG. 1. The panel (a) is a gel-filtration chromatogram of the purified WT ligase alone. The panel (b) is a gel-filtration chromatogram of the mixture of the WT ligase with nicked DNA substrate. A result of fractionating peaks (into portions 1 to 5) shown in the panel (b), followed by protein analysis by SDS-PAGE, is also shown in the same panel. The result obtained by using the DNA ligase mutant (ΔC25) is shown in panels (c), (d), and (e) in FIG. 1. The panel (c) is a gel-filtration chromatogram of the DNA ligase mutant alone. The panel (d) is a gel-filtration chromatogram of the mixture of the DNA ligase mutant (ΔC25) with nicked DNA substrate. A result of fractionating peaks (into portions 1 to 5) shown in the panel (d), followed by protein analysis by SDS-PAGE, is also shown in the same panel. Further, the panel (e) in FIG. 1 shows a chromatogram obtained by fractionating the central portion (indicated as "2" in the panel (d)) of this peak and applying a reaction solution reacted at 37° C. for 10 minutes after the addition of ATP (100 μg/ml) to the same gel-filtration column.

DETAILED DESCRIPTION OF THE INVENTION

The present inventors have conducted diligent studies in light of the situations and have consequently completed the present invention by finding out that a C-terminal helix portion of DNA ligase inhibits enzyme flexibility, thereby reducing the DNA-binding ability and that DNA-binding properties are improved by partially or completely deleting the C-terminal helix portion of the DNA ligase.

Namely, the present invention provides:

(1) a DNA ligase mutant obtained by partially or completely deleting a C-terminal helix portion of DNA ligase;

(2) the mutant according to (1), wherein the mutant lacks the C-terminal helix portion of the DNA ligase and 0 or 1 to 5 amino acids N-terminally adjacent thereto;

(3) the mutant according to (1) or (2), wherein the DNA ligase is derived from a thermophilic bacterium, hyperthermophilic bacterium, thermophilic archaebacterium, or hyperthermophilic archaebacterium;

(4) the mutant according to (3), wherein the DNA ligase is derived from *Pyrococcus furiosus;*

(5) DNA encoding a mutant according to any of (1) to (4);

(6) a vector incorporating therein DNA according to (5);

(7) a plasmid deposited as Deposition No. FERM P-20580 with National Institute of Advanced Industrial Science and Technology, International Patent Organism Depositary;

(8) a plasmid deposited as Deposition No. FERM P-20593 with National Institute of Advanced Industrial Science and Technology, International Patent Organism Depositary;

(9) a LCR method using a mutant according to any of (1) to (4); and

(10) a kit for LCR, comprising a mutant according to any of (1) to (4).

A first aspect of the present invention provides a DNA ligase mutant which partially or completely lacks a C-terminal helix portion. The "helix portion" refers to consecutive amino acids constituting the helix structure of an enzyme. Many DNA ligases have the helix portion at their C termini. Examples of the DNA ligase having the helix portion at the C terminus include those derived from human beings, yeast, and bacteria. The C-terminal helix portion is considered to make the enzyme structure rigid, on the other hand, inhibits enzyme flexibility, thereby reducing the DNA-binding ability, resulting in poor reactivity. Thus, the DNA-binding ability and reactivity of the enzyme may be improved by partially or completely deleting the C-terminal helix portion.

The DNA ligase used in the present invention may be any of those having the helix portion at the C terminus and may be derived from any origins. Taking into consideration improvement in the efficiency and specificity of the LCR method, it is preferred to use DNA ligase improved in both reactivity and thermostability. Therefore, preferably, the DNA ligase used for producing the mutant according to the present invention is derived from, for example a thermophile. The DNA ligase mutant having excellent DNA-binding ability and reactivity and thermostability may be obtained by partially or completely deleting the C-terminal helix portion of such thermostable ligase. Particularly preferable DNA ligase is derived from a thermophilic bacterium (e.g., *Bacillus stearothermophilus*), hyperthermophilic bacterium (e.g., *Thermotoga maritima*), thermophilic archaebacterium (e.g., *Thermoplasma volcanium*), or hyperthermophilic archaebacterium (e.g., *Aeropyrum pernix*). Most preferably, the DNA ligase is derived from the hyperthermophilic bacterium or hyperthermophilic archaebacterium. Most preferable DNA ligase is derived from *Pyrococcus furiosus*.

The C-terminal helix portion of the DNA ligase may be deleted partially or completely. Generally, the deletion is performed by deleting a certain number of consecutive amino acids from the C terminus of the enzyme. The deletion of the C-terminal helix portion may be performed using a method known by those skilled in the art and preferably, is performed by site-specific mutagenesis. For example, the insertion of a stop codon to the DNA ligase may delete the C-terminal amino acid sequence encoded by a sequence subsequent to the stop codon. In the present specification, for example, a mutant which lacks 25 amino acids of DNA ligase from the C terminus is also referred to as "ΔC25". If the amino acids deleted from the C terminus are too few in number (the deletion of the C-terminal helix portion is insufficient), molecular flexibility is not sufficiently obtained, resulting in insufficient improvement in the DNA-binding ability and reactivity of the enzyme. If the amino acids deleted from the C terminus are too large in number (too many amino acids N-terminally adjacent to the C-terminal helix portion are deleted), molecular flexibility is increased but the enzyme itself is instable, resulting in reduction in thermostability. The amino acids may be deleted from the C terminus of the enzyme so that there remain 0 to several N-terminal amino acids within the helix portion or so that the whole helix portion and 0 to several amino acids N-terminally adjacent thereto are deleted. The term "several amino acids" means herein 1 to 9 amino acids. It is preferred to delete the C-terminal helix portion together with amino acids in a region which is N-terminally adjacent to the C-terminal helix portion and which does not constitute the secondary structure of the enzyme. The deletion of the amino acids in the secondary structure-free region is considered to maintain the favorable conformation of the enzyme. For example, the whole helix portion and 0 or 1 to 5 amino acids N-terminally adjacent thereto may be deleted.

In a further aspect, the present invention provides DNA encoding the DNA ligase mutant and a vector incorporating the DNA therein. The DNA ligase mutant of the present invention may be produced by incorporating the DNA encoding the DNA ligase mutant of the present invention into a vector, which is in turn introduced into a host. Those skilled in the art may select a variety of vectors appropriate to the incorporated DNA and the host. DNA encoding the DNA ligase mutant derived from a bacterium may be incorporated into a bacterial plasmid. An *Escherichia coli* plasmid (e.g., pBR322 and pUC18) or *Bacillus subtilis* plasmid (e.g., pHY300PLK) is typically used as the bacterial plasmid.

Moreover, those skilled in the art may select and incorporate a suitable promoter (e.g., Lac, tac, trp, and actin promoters) or enhancer (e.g., CMV and SV40 enhancers) into a proper position in the vector according to a method known in the art in order to improve protein productivity. Examples of the plasmid capable of expressing such a DNA ligase mutant include pET21d-PfuLigDC25 and pET21d-PfuLigDC22 obtained by the present invention. These plasmids may be used to produce the DNA ligase mutant having excellent thermostability and DNA-binding ability and reactivity.

In a further aspect, the present invention provides a LCR method using the DNA ligase mutant of the present invention and a kit for LCR comprising the DNA ligase mutant of the present invention. As described above, the DNA ligase mutant, particularly the DNA ligase mutant having excellent thermostability, of the present invention exercises its power when used in the LCR method. Namely, the more specific and rapid LCR method as well as efficient gene amplification and point mutation detection may be achieved by using the DNA ligase mutant of the present invention having excellent thermostability and DNA-binding ability and reactivity. The kit for performing the LCR method comprises the DNA ligase mutant of the present invention as an essential component thereof. The kit is usually provided with an instruction manual.

The present invention will be described more fully with reference to Examples. However, the scope of the present invention is not intended to be limited to these Examples.

EXAMPLE 1

Preparation of C-Terminal Helix-Deleted DNA Ligase Mutant (1) Preparation of *P. furiosus* Genomic DNA

*P. furiosus* DSM3638 was obtained from Deutsche Sammlung von Mikroorganismen und Zelkullturen GmbH and cultured according to the method described in the article (Nucleic Acids Research, Vol. 21, p. 259-265). Approximately 1.2 g of bacterial cells were obtained from 500 ml of the culture solution. These bacterial cells were suspended in 10 ml of Buffer L (10 mM Tris-HCl (pH 8.0), 1 mM EDTA, and 100 mM NaCl) and supplemented with 1 ml of 10% SDS. After stirring, the resulting mixture was supplemented with 50 ml of proteinase K (20 mg/ml) and left undisturbed at 55° C. for 60 minutes. Then, the reaction solution was successively subjected to phenol extraction, phenol/chloroform extraction, and chloroform extraction and then supplemented with ethanol to insolubilize DNA. The collected DNA was dissolved in 1 ml of TE solution (10 mM Tris-HCl (pH 8.0) and 1 mM EDTA) and reacted at 37° C. for 60 minutes by the addition of 0.75 mg of RNase A. Then, the reaction solution was subjected again to phenol extraction, phenol/chloroform extraction, and chloroform extraction to collect DNA by ethanol precipitation. As a result, 0.75 mg of DNA was obtained.

(2) Cloning of Lig Gene

Primers for amplifying a putative lig gene region from the *P. furiosus* genomic DNA by PCR were designed. The primers used in 1st PCR: 5'-CTAGTGGATCTGATGCGT-TATCTGG-3' (SEQ ID NO: 9) and 5'-TCGGGACTATTGT-TAGACCTTAGC-3' (SEQ ID NO: 10) were synthesized. The primers used in 2nd PCR: 5'-GGCCATGGGTTATCTG-GAGCTTGCTCAAC-3 (SEQ ID NO: 11) and 5'-GCG-GATCCTTAGCTTTCCACTTTTCTTTCATC-3' (SEQ ID NO: 12) were prepared so as to anneal at positions internal to the respective first primers. A NcoI recognition sequence was incorporated into the forward primer in accordance with the putative translation initiation codon "ATG" of the lig gene. A BamHI recognition sequence was introduced immediately after the stop codon into the reverse primer. PyroBEST DNA Polymerase (Takara-Bio) was used to amplify the gene of interest under PCR conditions to perform 30 cycles of thermal denaturation at 95° C., annealing at 55° C., and elongation at 72° C. The 1st PCR product was used as a template to perform 2nd PCR under the same conditions. The resulting product was incorporated into PGEM-T Easy vector (Promega). A DNA sequencer (Beckman Coulter) was used to confirm the nucleotide sequence of the inserted fragment region. Then, the lig gene cleaved from the pGEM-T Easy vector by NcoI-BamHI cleavage was inserted into pET21d vector (EMD Bioscience) to obtain a plasmid pET21d-lig. Since the NcoI sequence was introduced into the initiation codon site in order to construct this expression system, the second codon "agg" shown in SEQ ID NO: 1 was changed to "ggt" to convert the second amino acid of the obtained translation product from the original "Arg" to "Gly" (see SEQ ID NOs: 3 and 4).

For using this plasmid pET21d-lig as a template to produce mutants (ΔC22 and ΔC25) lacking C-terminal 22 and 25 residues, a method of introducing a stop codon to the residues (22nd and 25th residues from the C termini) was adopted. A primer set for producing ΔC22: 5'-CCAGAAGATGCATAAACAATAGAGAGAATC-3' (SEQ ID NO: 13) and 5'-GATTCTCTCTATTGTTTATGCATCTTCTGG-3 (SEQ ID NO: 14) and PyroBEST DNA Polymerase (Takara-Bio) were used to amplify the gene of interest under PCR conditions to perform 20 cycles of thermal denaturation at 95° C., annealing at 55° C., and elongation at 72° C. Alternatively, a primer set for producing ΔC25: 5'-GATAAAGGACCATAAGATGCAGATACAATA-3' (SEQ ID NO: 15) and 5'-TATTGTATCTGCATCTTATGGTCCTTTATC-3' (SEQ ID NO: 16) were used to amplify the gene of interest by the same approach.

(3) Construction and Purification of Large-Scale Expression Systems of *P. furiosus*-Derived Native Ligase and C-terminal Helix-Deleted Ligase Mutants (ΔC22 and ΔC25)

Hereinafter, the construction and purification of a large-scale expression system of untreated (native) ligase will be described. The C-terminal helix-deleted ligase mutants (ΔC22 and ΔC25) could be expressed and generated in large amounts in exactly the same way as for the WT ligase except that the initially used plasmid was changed to pET21d-ligDC22 and pET21d-ligDC25 (stop codon was introduced to the 22nd and 25th residues, respectively, from the C terminus).

The plasmid pET21d-lig was transformed into a competent cell Stratagene BL21 Codonplus-RIL, which was in turn cultured at 37° C. in Luria-Bertani medium in the presence of 100 μg.mL$^{-1}$ ampicillin and 20 μg.mL$^{-1}$ chloramphenicol. At the point in time when the turbidity of the culture solution (absorbance at 660 nm) reached 0.6, isopropyl-β-D-thiogalactopyranoside was added at the final concentration of 1 mM to induce protein expression. After additional 6-hour culture, the bacterial cells were collected with a centrifuge. The bacterial cells were suspended into a Tris-HCl buffer (pH 8) and disrupted by sonication, followed by centrifugation. The supernatant was heat-treated at 80° C. for 20 minutes, followed by centrifugation. Polyethyleneimine was added at the final concentration of 0.15% (w/v) to the supernatant, followed by centrifugation to remove the nucleic acid component. This solution was supplemented with ammonium sulfate to achieve 80% saturation. The resulting mixture was centrifuged to collect a pellet.

The pellet was dissolved in a Tris-HCl buffer (pH 8) and subjected to separation procedures using affinity chromatography (HiTrap Heparin, 5 ml; Amersham Pharmacia Biotech) to collect a fraction eluted with 0.4 to 0.5 M NaCl. This fraction was further subjected to separation procedures using anion exchange chromatography (HiTrap Q, 5 ml; Amersham Pharmacia Biotech) to collect a pass-through fraction. This solution was concentrated and subjected to separation procedures using a gel-filtration column (Superdex 200 HiLoad 26/60; Amersham Pharmacia Biotech) at a flow rate 2 ml/min to collect a main peak eluted around 100 minutes. When this solution was electrophoresed, the DNA ligase mutants could be confirmed to have 99% or more purity in terms of protein purity and have a molecular weight smaller than the native protein by the C-terminally deleted portion. As described above, it was demonstrated that the DNA ligase mutant of the present invention is obtained easily.

The nucleotide sequence of DNA encoding natural DNA ligase of *Pyrococcus furiosus* is shown in SEQ ID NO: 1, and the amino acid sequence of a protein encoded thereby is shown in SEQ ID NO: 2. The C-terminal helix of the DNA ligase of *Pyrococcus furiosus* is composed of an amino acid sequence from "Asp" at position 540 to "Ser" at position 561 in SEQ ID NO: 2. The nucleotide sequence of DNA encoding the WT DNA ligase obtained in Example 1 is shown in SEQ ID NO: 3, and the amino acid sequence of a protein encoded thereby is shown in SEQ ID NO: 4. The nucleotide sequence encoding the mutant ΔC25 obtained in Example 1 is shown in SEQ ID NO: 5, and the amino acid sequence of a protein encoded thereby is shown in SEQ ID NO: 6. The nucleotide sequence encoding the mutant ΔC22 obtained in Example 1 is shown in SEQ ID NO: 7, and the amino acid sequence of a protein encoded thereby is shown in SEQ ID NO: 8.

The plasmid pET21d-LigDC25 containing the DNA encoding the mutant ΔC25 obtained in the present invention was deposited as Deposition No. FERM P-20580 with National Institute of Advanced Industrial Science and Technology, International Patent Organism Depositary on Jul. 1, 2005. The plasmid pET21d-LigDC22 containing the DNA encoding the mutant ΔC22 obtained in the present invention was deposited as Deposition No. FERM P-20593 with National Institute of Advanced Industrial Science and Technology, International Patent Organism Depositary on Jul. 14, 2005.

EXAMPLE 2

DNA-Binding Ability of C-Terminal Helix-Deleted DNA Ligase Mutant

The interaction between the native ligase or the C-terminal helix-deleted mutant DNA ligase (ΔC25) obtained in Example 1 and 5'-phosphorylated nicked DNA was analyzed by gel-filtration chromatography to examine the substrate-biding ability of the DNA ligase mutant.

The 5'-phosphorylated single-stranded DNA was used to measure the binding ability between the DNA and the ligase. The DNA sequence was 5'P-TATAGCGAAGCTATATA GCGAAGCTATA-3' (SEQ ID NO: 17). The underlined parts are known to assume a stable hairpin structure (Nucleic Acids Research, Vol. 22, p. 2217-2221), and this single-stranded DNA was considered to serve as a stable nicked substrate. The DNA was dissolved in a buffer (10 mM Tris-HCl (pH 8.0) and 100 mM NaCl), then heated at 98° C. for 5 minutes with a thermal cycler, and gradually cooled to room temperature. This solution was applied to a gel-filtration column to sepa rate a substrate of size consisting of only the single-stranded DNA, which was in turn used in subsequent analysis. This substrate DNA was subjected to native electrophoresis along with double-stranded DNA of the corresponding size to reconfirm that the nicked substrate derived from the single strand was formed.

This substrate DNA was mixed with the ligase at a molar ratio of 1.2:1.0 (each concentration is approximately 1 nM) in a buffer (50 mM Tris-HCl (pH 8.0), 100 mM NaCl, 10% (v/v), and 1 MM MgCl$_2$). The mixture was left undisturbed at 25° C. for 5 minutes and then concentrated to 10 µl by the centrifugation of a ultrafilter, followed by gel-filtration chromatography analysis. The gel-filtration analysis was performed using SMART system (Amersham Pharmacia) equipped with Superdex 200 (Amersham Pharmacia) column. The absorbance at wavelengths of 260 and 280 nm of a solution passing thorough the column was continuously monitored, and a fraction exhibiting an absorbance peak was electrophoresed to clarify the composition thereof (FIG. 1).

The result obtained by using the WT ligase is shown in panels (a) and (b) in FIG. 1. The panel (a) is a gel-filtration chromatogram of the purified WT ligase alone. The panel (b) is a gel-filtration chromatogram of the mixture of the WT ligase with the nicked DNA substrate. The result obtained by using the DNA ligase mutant (ΔC25) is shown in panels (c), (d), and (e) in FIG. 1. The panel (c) is a gel-filtration chromatogram of the DNA ligase mutant (ΔC25) alone. The panel (d) is a gel-filtration chromatogram of the mixture of the DNA ligase mutant with the nicked DNA substrate. When the panel (d) was compared to the panel (c), a large peak was seen in a higher molecular weight zone in the panel (d), and the absorbance at 260 nm and the absorbance at 280 nm overlapped each other. This showed that the DNA ligase mutant (ΔC25) took up the substrate DNA. Thus, the substrate DNA was bound to the DNA ligase mutant. SDS-PAGE for examining proteins in the peak also exhibited a particularly highly colored protein band in the lane 2 using the central portion (indicated as "2") of the peak as a sample. On the other hand, in the panel (b), the corresponding peak in a higher molecular weight zone was quite small, indicating that the substrate DNA was hardly bound to the WT ligase. The panel (e) in FIG. 1 further shows a chromatogram obtained by fractionating the central portion (indicated as "2") of this peak in the higher molecular weight zone in the panel (d) and applying a reaction solution reacted at 37° C. for 10 minutes after the addition of ATP (100 µg/ml) to the same gel-filtration column. The main component of each peak is shown in this panel. The panel shows the dissociation of DNA bonded with the enzyme and the progression of the reaction.

EXAMPLE 3

Thermostability of DNA Ligase Mutant of the Present Invention

Both the WT and mutant DNA ligases used in Example 2 were heat-treated at 85° C. for 20 minutes for the purpose of intentionally denaturing non-thermostable proteins at the initial stage of purification and simplifying subsequent purification procedures. In the heat treatment, the mutant exhibited thermostability comparable to that of the native.

According to the present invention, a DNA ligase mutant improved in binding ability and reactivity with DNA and further in thermostability is obtained. Therefore, the present invention is available in a biochemical research field, research reagent field, diagnostic reagent field, pharmaceutical field, and so on.

ADVANTAGES OF THE INVENTION

The present invention provides a DNA ligase mutant having DNA-binding ability and reactivity more excellent than those of WT DNA ligase. When an enzyme derived from a thermophile is used, a DNA ligase mutant having excellent DNA-binding ability and reactivity and thermostability is obtained. The present invention further provides DNAs encoding these DNA ligases, a LCR method using the DNA ligase, and a kit for the LCR method. Thus, the more specific and rapid LCR method as well as efficient gene amplification and point mutation detection may be achieved. Gene manipulation in a system with high selectivity may be performed by using the DNA ligase mutant of the present invention.

It should be further understood by those skilled in the art that although the foregoing description has been made on embodiments of the invention, the invention is not limited thereto and various changes and modifications may be made without departing from the spirit of the invention and the scope of the appended claims.

Sequence Listing Free Text

SEQ ID NO: 1 shows a nucleotide sequence encoding native *Pyrococcus furiosus* DNA ligase.

SEQ ID NO: 2 shows an amino acid sequence of native *Pyrococcus furiosus* DNA ligase.

SEQ ID NO: 3 shows a nucleotide sequence encoding native *Pyrococcus furiosus* DNA ligase obtained in Example 1.

SEQ ID NO: 4 shows an amino acid sequence of native *Pyrococcus furiosus* DNA ligase obtained in Example 1.

SEQ ID NO: 5 shows a nucleotide sequence encoding a *Pyrococcus furiosus* DNA ligase mutant (ΔC25) obtained in Example 1.

SEQ ID NO: 6 shows an amino acid sequence of a *Pyrococcus furiosus* DNA ligase mutant (ΔC25) obtained in Example 1.

SEQ ID NO: 7 shows a nucleotide sequence encoding a *Pyrococcus furiosus* DNA ligase mutant (ΔC22) obtained in Example 1.

SEQ ID NO: 8 shows an amino acid sequence of a *Pyrococcus furiosus* DNA ligase mutant (ΔC22) obtained in Example 1.

SEQ ID NO: 9 shows a primer used in 1st PCR for amplifying DNA encodong native *Pyrococcus furiosus* DNA ligase.

SEQ ID NO: 10 shows a primer used in 1st PCR for amplifying DNA encodong native *Pyrococcus furiosus* DNA ligase.

SEQ ID NO: 11 shows a primer used in 2nd PCR for amplifying DNA encodong native *Pyrococcus furiosus* DNA ligase.

SEQ ID NO: 12 shows a primer used in 2nd PCR for amplifying DNA encodong native *Pyrococcus furiosus* DNA ligase.

SEQ ID NO: 13 shows a primer for amplifying DNA encodong a *Pyrococcus furiosus* DNA ligase mutant (ΔC22).

SEQ ID NO: 14 shows a primer for amplifying DNA encodong a *Pyrococcus furiosus* DNA ligase mutant (ΔC22).

SEQ ID NO: 15 shows a primer for amplifying DNA encodong a *Pyrococcus furiosus* DNA ligase mutant (ΔC25).

SEQ ID NO: 16 shows a primer for amplifying DNA encodong a *Pyrococcus furiosus* DNA ligase mutant (ΔC25).

SEQ ID NO: 17 shows a nucleotide sequence encoding a substrate for native *Pyrococcus furiosus* DNA ligase and a mutant thereof.

The invention claimed is:

1. A DNA ligase mutant having the amino acid sequence of SEQ ID NO:6, said DNA ligase mutant having enhanced binding to DNA and enhanced enzymatic activity, as compared with wild-type, non-mutant DNA ligase.

2. A ligation chain reaction (LCR) method using the mutant according to claim 1.

3. A kit for LCR, comprising the mutant according to claim 1.

* * * * *